United States Patent [19]

Nomoto et al.

[11] 4,309,354
[45] Jan. 5, 1982

[54] CHROMONE DERIVATIVES

[75] Inventors: Seiichiro Nomoto; Hironori Ikuta, both of Tokyo; Yoshimasa Machida, Wako; Shigeto Negi, Kodaira; Isao Sugiyama, Tokyo; Hiroshi Yamauchi, Gifu; Kenro Nakatsuka, Matsudo; Isao Saito, Aza-Sori, all of Japan

[73] Assignee: Eisai Co., Ltd., Tokyo, Japan

[21] Appl. No.: 218,403

[22] Filed: Dec. 19, 1980

[30] Foreign Application Priority Data

Oct. 7, 1980 [JP] Japan .............................. 55-139269

[51] Int. Cl.³ .......................................... C07D 311/22
[52] U.S. Cl. .................................. 260/345.2; 544/27; 544/28; 260/463
[58] Field of Search ..................................... 260/345.2

[56] References Cited
U.S. PATENT DOCUMENTS 3,904,618  9/1975  Pioch .............................. 260/345.2

Primary Examiner—Nicky Chan
Attorney, Agent, or Firm—Wenderoth, Lind & Ponack

[57] ABSTRACT

New chromone derivatives having the formula:

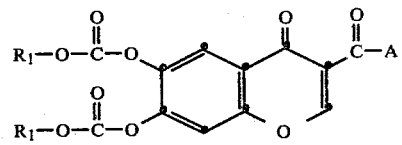

wherein A represents a hydrogen atom, a halogen atom or a hydroxyl group, and $R_1$ represents a lower alkyl or a chloro-substituted lower alkyl group. The derivatives are useful intermediates for synthesis of cephem derivatives as antibacterial drugs.

4 Claims, No Drawings

CHROMONE DERIVATIVES

This invention relates to new chromone derivatives having the formula (I):

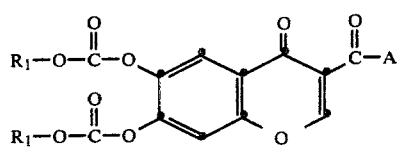
(I)

wherein A represents a hydrogen atom, a halogen atom or a hydroxyl group, and $R_1$ represents a lower alkyl, a chlorosubstituted lower alkyl group.

As a halogen atom in the formula (I), there are mentioned chlorine atom, bromine atom, and the like. As a lower alkyl group, there are mentioned methyl, ethyl, propyl, and the like. As a chloro-substituted lower alkyl group, there are mentioned 2,2,2-trichloroethyl group and the like, for example.

It has been found by the inventors of this invention that the new compounds of the formula (II)

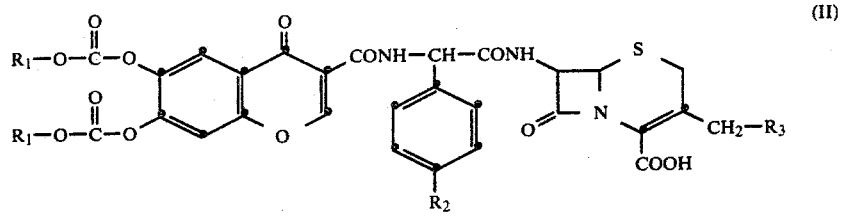
(II)

wherein $R_1$ has the same meanings as defined above, $R_2$ represents a hydrogen atom or a hydroxyl group, and $R_3$ represents a lower alkanoyloxy group or a nitrogen-containing heterocyclic thio group, possess remarkable properties as antibacterial drugs.

The compound of this invention is useful as an intermediate for synthesis of the above compound (II). More particularly, the above compound (II) can be synthesized by the use of the compound of this invention as shown in the following scheme:

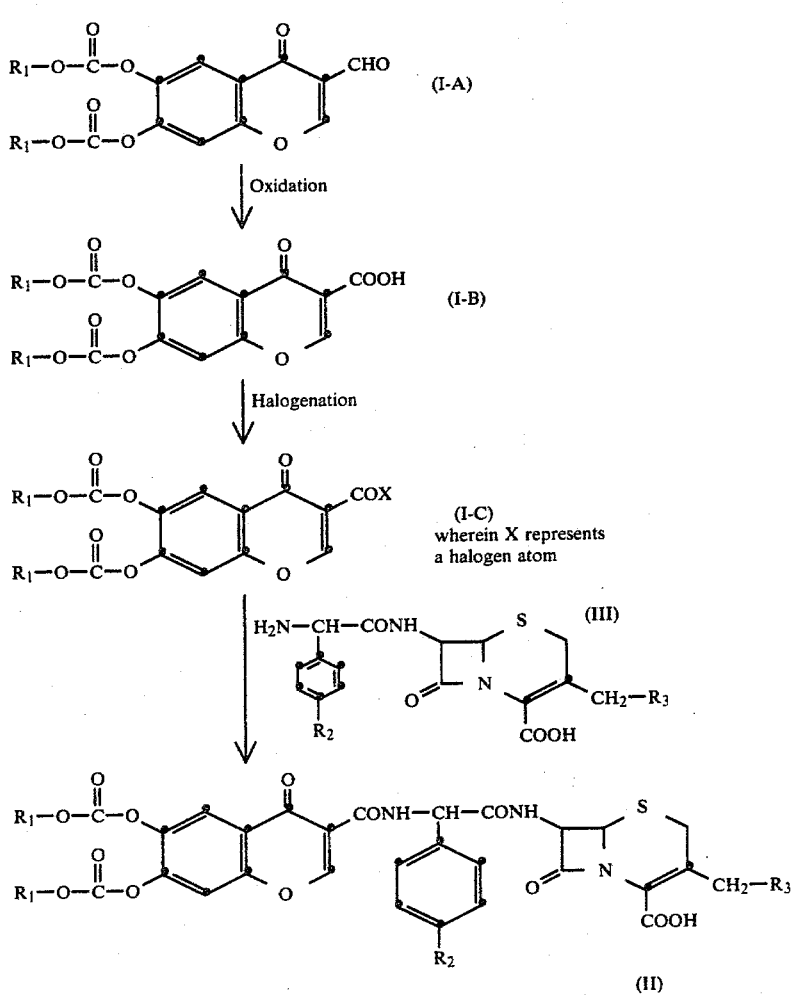

As another route, the compound of the formula (II) can be produced by means of a one-pot reaction through the acid bromide as an intermediate, starting from the aldehyde of the formula (I-A) as mentioned above.

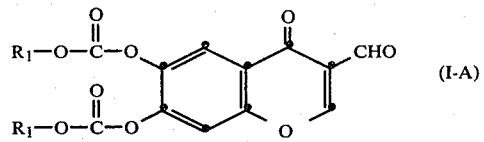
(I-A)

↓ N-Bromosuccinimide
hν (Light)

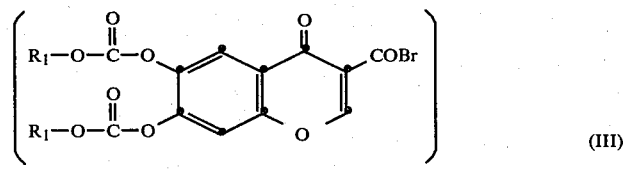
(III)

↓ H₂N—CH—COHN ... (reagent shown)

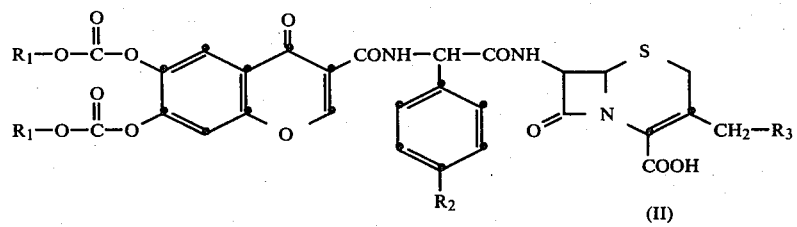
(II)

As the other route, the compound of the formula (II) can be synthesized by reacting the carboxylic acid of the formula (I-B) with the compound of the formula (III), in the presence of a condensing agent such as N,N′-dicyclohexylcarbodiimide, N,N′-diethylcarbodiimide, N-cyclohexyl-N′-morphorinoethylcarbodiimide, polyphosphoric acid ethyl ester, tosyl chloride, ethylchloroformate, phosphorus oxychloride, oxalyl chloride, and the like.

The compound (I) of this invention can be prepared by means of the following procedures.

(1) A compound represented by the formula:

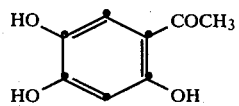
(IV)

is reacted with a chloroformic ester represented by the formula:

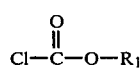
(V)

wherein $R_1$ is as defined hereinabove, to obtain a compound represented by the formula:

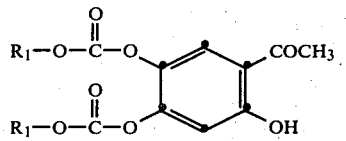
(VI)

wherein $R_1$ is as defined above.

(2) The compound of the formula (VI) is reacted with dimethyl formamide in the presence of an acid halide to obtain a compound of this invention represented by the formula:

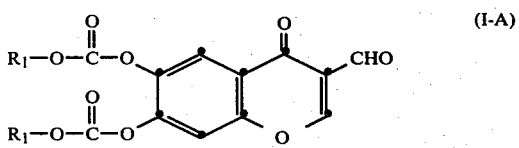
(I-A)

wherein $R_1$ is as defined above.

(3) The compound of the formula (I-A) is oxidized in the presence of an oxidizing agent to obtain a compound of this invention represented by the formula:

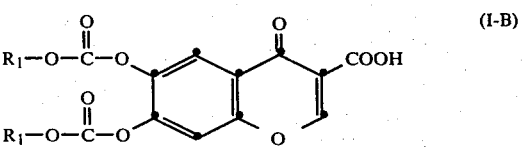
(I-B)

wherein $R_1$ is as defined above.

(4) A compound represented by the formula:

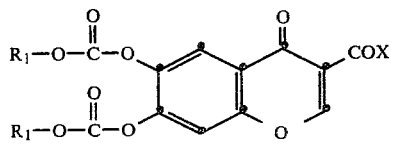

wherein $R_1$ and X are as defined above, can be obtained by reacting the compound of the formula (I-B) above with a halogenating agent.

In the above reaction, the reaction of the compound of the formula (IV) with the compound of the formula (V) in step (1) can be carried out in the presence of a base such as pyridine, triethylamine or N-methylmorpholine at a temperature of preferably below room temperature.

The reaction of the compound of the formula (VI) with dimethyl formamide in step (2) can be carried out by using an inert solvent such as benzene, toluene, ethyl ether, tetrahydrofuran or dioxane or an excessive amount of dimethyl formamide, the reactant, instead of the solvent. Examples of the acid halide are phosphorus oxychloride, thionyl chloride, phosgene, trichloromethyl chloroformate, phosphorus pentachloride, benzoyl chloride and p-toluenesulfonyl chloride.

Oxidation of the compound of the formula (I-A) in step (3) is carried out using a chlorite-chlorine scavenger, a Jones reagent (chromic anhydride-sulfuric acid), sodium bichromate-sulfuric acid, etc. as an oxidizing agent.

Of the above oxidizing agents, the chlorite-chlorine scavenger system is most preferred in view of the yield of the product. Sodium chlorite and potassium chlorite may be cited as examples of the chlorite. The chlorine scavenger denotes a compound having the action of scavenging chlorine generated in the reaction system, and examples are sulfamic acid, resorcinol and pyroglutamic acid. Sulfamic acid is most preferred. The oxidation reaction is carried out usually at $-10°$ to $40°$ C., preferably $10°$ to $20°$ C. Examples of the reaction solvent are non-hydrophilic solvents such as dichloromethane, chloroform, dichloroethane, ethyl acetate, benzene and toluene and hydrophilic solvents such as acetone, dioxane, tetrahydrofuran and acetonitrile.

An ordinary halogenating agent may be used as the halogenating agent for the preparation of the compound of the formula (I-C) in step (4). For example, to obtain an acid chloride, phosphorus pentachloride, thionyl chloride, and the like may be cited.

The following Examples and Preparations illustrate the present invention in detail.

EXAMPLE 1

6,7-Bis(ethoxycarbonyloxy)chromone-3-carboxaldehyde

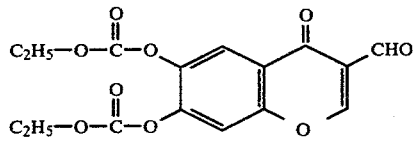

(a) 4,5-Bis(ethoxycarbonyloxy)-2-hydroxyacetophenone 2,4,5-Trihydroxyacetophenone (3.36 g) was dissolved in 150 ml of ethyl acetate, and 3.24 ml of pyridine was added at about $-5°$ C. with stirring. Then, 50 ml of a solution of 3.8 ml of ethyl chloroformate in ethyl acetate was added dropwise over 30 minutes. The mixture was stirred for 10 minutes at the same temperature. The resulting precipitate was collected by filtration and washed three times with 10 ml of ethyl acetate. The washings and the filtrate were combined, and the mixture was washed with water (once) and a saturated aqueous solution of sodium chloride (three times) and dried over magnesium sulfate. The solvent was distilled off, and the residue was recrystallized from ethyl ether-ethanol. The crystals were collected by filtration, and washed with ethanol and n-hexane and dried to afford 4.60 g of the desired product.

Melting point: $58°-60°$ C.

(b) 6,7-Bis(ethoxycarbonyloxy)chromone-3-carboxaldehyde

The above compound a (37.47 g) was dissolved in 300 ml of dimethyl formamide. The solution was cooled to about $-5°$ C., and with stirring, 120 ml of phosphorus oxychloride was added dropwise over 40 minutes. The mixture was stirred at room temperature for 5.5 hours. The reaction mixture was added to 3 liters of ice water, and stirred for 20 minutes. The resulting precipitate was collected by filtration, washed with water, and dissolved in ethyl acetate. The ethyl acetate solution was washed with water three times and dried over magnesium sulfate. The solvent was distilled off, and ethanol was added to the residue to solidify it. The solidified product was collected by filtration, washed with ethanol and n-hexane, and then dried to afford 28.5 g of the desired product.

Melting point: $101°-102°$ C.

Mass spectrum (m/e): 350 (M+)

Elemental analysis for $C_{16}H_{14}O_9$:

|  | C | H |
| --- | --- | --- |
| Calculated (%): | 54.86 | 4.03 |
| Found (%): | 54.70 | 3.81 |

Infrared absorption spectrum (cm$^{-1}$, nujol):
1775, 1765, 1700, 1660, 1625.

NMR spectrum ($\delta$, CDCl$_3$):
1.45 (6H, t, J=7 Hz), 4.40 (4H, q, J=7 Hz),
7.62 (1H, s), 8.17 (1H, s),
8.53 (1H, s), 10.33 (1H, s).

EXAMPLE 2

6,7-Bis(ethoxycarbonyloxy)chromone-3-carboxylic acid

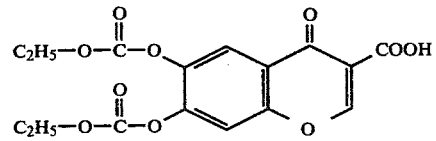

The compound (1.05 g) obtained in (b) of Example 1 was dissolved in 31.5 ml of dichloromethane, and a solution of 1.05 g of sulfamic acid in 18.9 ml of water was added at 10° C. with stirring. Then, a solution of 525.6 mg of sodium chlorite in 1.2 ml of water was added. The solution was stirred at the same temperature for 1 hour, and allowed to separate. The dichloromethane layer was washed with water (once) and then with a saturated aqueous solution of sodium chloride (twice), and dried over magnesium sulfate. The solvent was distilled off, and ethyl ether was added to the residue to solidify it. The solidified product was collected by filtration, and dried to afford 950 mg of the desired product.

Melting point: 107°–109° C.
Mass spectrum (m/e): 366 (M+)
Elemental analysis for $C_{16}H_{14}O_{10}$:

|  | C | H |
|---|---|---|
| Calculated (%): | 52.47 | 3.85 |
| Found (%): | 52.57 | 3.63 |

Infrared absorption spectrum (cm$^{-1}$, nujol):
1765, 1625.
NMR spectrum (δ, CDCl$_3$):
1.38 (6H, t, J=7 Hz), 4.37 (4H, q, J=7 Hz),
7.74 (1H, s), 8.21 (1H, s), 8.98 (1H, s).

EXAMPLE 3

6,7-Bis(ethoxycarbonyloxy)chromone-3-carbonyl chloride

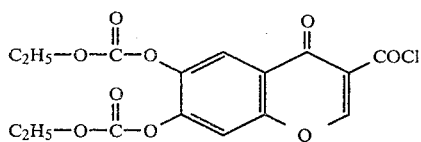

The compound (1.1 g) of Example 2 was dissolved in 20 ml of benzene, and 2 ml of thionyl chloride was added dropwise at room temperature with stirring. Then, the mixture was refluxed with stirring. The reaction mixture was concentrated, and n-hexane was added to the concentrate to crystallize it. The resulting crystals were collected by filtration, washed with n-hexane an dried to afford 980 mg of the desired product.

Melting point: 89°–92° C.
Mass spectrum (m/e): 384 (M+), 386 (M+).
Infrared absorption spectrum (cm$^{-1}$, nujol):
1770, 1680, 1620, 1565.

EXAMPLE 4

6,7-Bis(2,2,2-trichloroethoxycarbonyloxy)chromone-3-carboxaldehyde

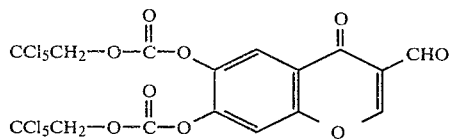

(a) 2-Hydroxy-4,5-bis(2,2,2-trichloroethoxycarbonyloxy)-acetophenone 2,4,5-Trihydroxyacetophenone (16.8 g) was dissolved in 500 ml of ethyl acetate, and 15.98 ml of pyridine was added at about −5° C. with stirring. Then, a solution of 26.82 ml of 2,2,2-trichloroethyl chloroformate in 70 ml of ethyl acetate was added dropwise over the course of 2.5 hours. The mixture was stirred at the same temperature for 15 minutes. The precipitate formed was collected by filtration and washed with ethyl acetate. The washing and the filtrate were combined, and the mixture was washed with water (once) and a saturated aqueous solution of sodium chloride (twice), and dried over magnesium sulfate. The solvent was distilled off, and the residue was recrystallized from ethyl ether-ethanol. The crystals were collected by filtration, washed with ethanol and n-hexane and dried to afford 43.6 g of the desired product.

Melting point: 107.5°–108° C.

(b) 6,7-Bis(2,2,2-trichloroethoxycarbonyloxy)chromone-3-carboxaldehyde

The compound (25.95 g) obtained in (a) above was dissolved in 125 ml of dimethyl formamide. The solution was cooled to about −5° C., and with stirring, 50 ml of phosphorus oxychloride was added dropwise over 1 hour. The mixture was stirred at room temperature for 5.5 hours. The reaction mixture was added to 1.5 liters of ice water, and stirred for 20 minutes. The precipitate formed was collected by filtration, and washed with water. The product was dissolved in ethyl acetate, washed with water and dried over magnesium sulfate. The solvent was distilled off, and ethanol was added to the residue to solidify it. The solidified product was collected by filtration, washed with ethanol and then with n-hexane, and dried to afford 18.5 g of the desired product.

Melting point: 153°–155° C.
Mass spectrum (m/e):
554 (M+), 556 (M+), 558 (M+), 560 (M+).
Elemental analysis for $C_{10}H_8Cl_6O_9$:

|  | C | H |
|---|---|---|
| Calculated (%): | 34.51 | 1.45 |
| Found (%): | 34.63 | 1.47 |

Infrared absorption spectrum (cm$^{-1}$, nujol):
1780, 1720, 1693, 1660, 1626, 1566.
NMR spectrum (δ, CDCl$_3$):
4.92 (4H, s), 7.68 (1H, s),
8.27 (1H, s), 8.55 (1H, s),
10.36 (1H, s)

EXAMPLE 5

6,7-Bis(2,2,2-trichloroethoxycarbonyloxy)chromone-3-carboxylic acid

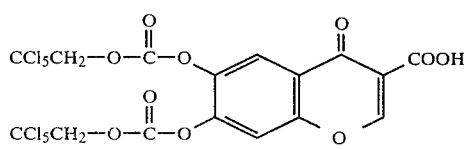

The compound (838.4 mg) obtained in Example 4, (b) was dissolved in 16 ml of dichloromethane, and with stirring at 10° C., a solution of 525 mg of sulfamic acid in 9.5 ml of water was added, followed by addition of a solution of 262.8 mg of sodium chlorite in 0.6 ml of water. The mixture was stirred for 1 hour at the same temperature. The reaction mixture was allowed to separate. The dichloromethane layer was washed with water and then with a saturated aqueous solution of sodium chloride, and then dried over magnesium sulfate. The solvent was distilled off, and the residue was recrystallized from ethyl ether to afford 685 mg of the desired product.

Melting point: 166°–167° C.
Mass spectrum (m/e):
570 (M+), 572 (M+), 574 (M+), 576 (M+)
Elemental analysis for $C_{16}H_8Cl_6O_{10}$:

| | C | H |
|---|---|---|
| Calculated (%): | 33.54 | 1.41 |
| Found (%): | 33.46 | 1.35 |

Infrared absorption spectrum (cm$^{-1}$, nujol):
1780, 1620, 1590, 1570.
NMR spectrum (δ, CDCl$_3$):
4.92 (4H, s), 7.80 (1H, s),
8.31 (1H, s), 9.02 (1H, s),
12.97 (1H, br. s).

EXAMPLE 6

6,7-Bis(2,2,2-trichloroethoxycarbonyloxy)chromone-3-carbonyl chloride

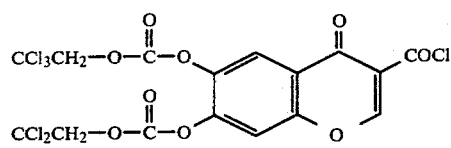

The compound (57.3 mg) obtained in Example 5 was dissolved in 10 ml of benzene, and with stirring at room temperature, 0.5 ml of thionyl chloride was added. The mixture was refluxed for 3 hours with stirring. The reaction mixture was concentrated, and 5 ml of n-hexane was added to the concentrate to crystallize it. The resulting crystals were collected by filtration, washed with n-hexane and dried to afford 34.8 mg of the desired product.
Melting point: 140° to 142° C.
Mass spectrum (m/e):
590 (M+), 592 (M+), 594 (M+), 596 (M+).
Infrared absorption spectrum (cm$^{-1}$, nujol):
1765, 1655, 1620, 1565.
Preparation 1
7β-[D-2-[6,7-Bis(ethoxycarbonyloxy)chromone-3-carboxamide]-2-(4-hydroxyphenyl)acetamide]-3-[(1-carboxymethyl-5-tetrazolyl)thiomethyl]-3-cephem-4-carboxylic acid 4-carboxylic acid trifluroacetic acid salt (0.318 g) was suspended in 5 ml of tetrahydrofuran. To the suspension was added 0.56 ml of N,O-bis(trimethylsilyl)acetamide at 0° C. with stirring. The mixture was stirred at the same temperature for 30 minutes. The acid chloride (192 mg) obtained in Example 3 was dissolved in 2 ml of tetrahydrofuran, and the solution was added. The mixture was stirred at 0° C. for 1 hour. The reaction mixture was concentrated to about 5 ml. The concentrate was added to 75 ml of 0.25 N hydrochloric acid cooled with ice. The precipitate formed was collected by filtration, washed with water and dried to afford 0.431 g of the desired product.
Melting point: 158°–163° C. (decomp.)
Elemental analysis for C$_{35}$H$_{31}$N$_7$O$_{16}$S$_2$:

| | C | H | N |
|---|---|---|---|
| Calculated (%): | 48.33 | 3.59 | 11.27 |
| Found (%): | 47.71 | 3.79 | 10.58 |

Infrared absorption spectrum (cm$^{-1}$, nujol):
1770, 1660, 1610.
NMR spectrum (δ, DMSO-d$_6$):
1.31 (6H, t, J=7 Hz), 3.52 (1H, d, J=18 Hz),
3.64 (1H, d, J=18 Hz), 4.08–4.56 (6H, m),
4.97 (1H, d, J=4.5 Hz), 5.28 (2H, s),
5.60–5.82 (2H, m), 6.71 (2H, d, J=8 Hz),
7.25 (2H, d, J=8 Hz), 8.02 (1H, s),
8.18 (1H, s), 9.02 (1H, s),
9.36 (1H, d, J=8 Hz), 9.95 (1H, d, J=8 Hz)
Antibacterial activity (MIC, μg/ml):

| | |
|---|---|
| Staph. aureus 209-P | 6.25 |
| Escher. coli NIJH | 0.4 |
| Kleb. pneumoniae EK-6 | ≦0.05 |
| Proteus morganii EP-14 | 1.56 |
| Pseud. aeruginosa EP172 | 0.8 |
| Ser. Marcescens ES-75 | ≦0.05 |

Preparation 2
7β-[D-2-[6,7-Bis(2,2,2-trichloroethoxycarbonyloxy)-chromone-3-carboxamide]-2-(4-hydroxyphenyl)acetamide]-3-[(1-carboxymethyl-5-tetrazolyl)thiomethyl]-3-cephem-4-carboxylic acid

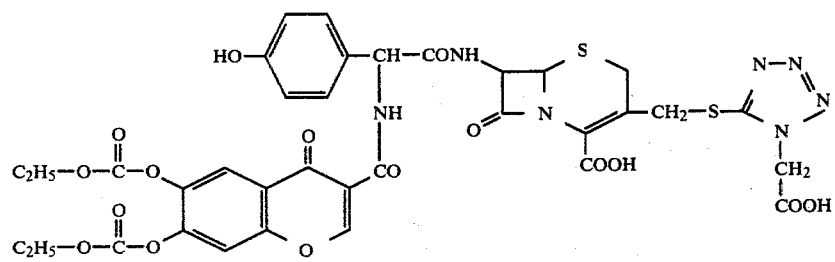

7β-[D-2-Amino-2-(4-hydroxyphenyl)acetamide]-3-[(1-carboxymethyl-5-tetrazolyl)thiomethyl]-3-cephem-

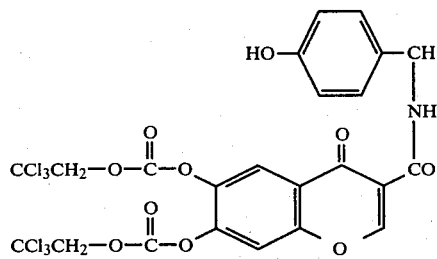

7β-[D-2-Amino-2-(4-hydroxyphenyl)acetamide]-3-[(1-carboxymethyl-5-tetrazolyl)thiomethyl]-3-cephem-4-carboxylic acid trifluoroacetic acid salt (0.318 g) was

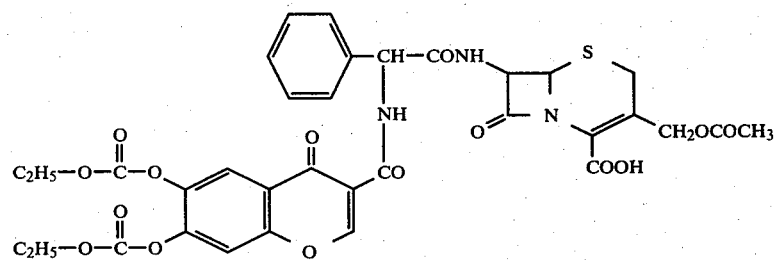

7β-[D-2-[6,7-Bis(ethoxycarbonyloxy)chromone-3-carboxamide]-2-phenylacetamide]-3-acetoxymethyl-3-cephem-4-carboxylic acid suspended in 10 ml of tetrahydrofuran. To the suspension was added 0.62 ml of N,O-bis(trimethylsilyl)acetamide at 0° C. with stirring, and the mixture was stirred at the same temperature for 30 minutes. A solution of 296 mg of the acid chloride obtained in Example 6 in 2 ml of tetrahydrofuran was added, and the mixture was stirred at 0° C. for 1 hour. The reaction mixture was added to 70 ml of 0.5 N hydrochloric acid cooled with ice. The resulting precipitate was collected by filtration, washed with ice water, and dried to afford 0.528 g of the desired product.

Melting point: 170°–175° C. (decomp.)
Elemental analysis for $C_{35}H_{25}Cl_6N_7O_{16}S_2$:

|  | C | H | N |
|---|---|---|---|
| Calculated (%): | 39.05 | 2.34 | 9.11 |
| Found (%): | 39.25 | 2.68 | 8.12 |

Infrared absorption spectrum (cm$^{-1}$, nujol):
1780, 1670, 1615.
NMR spectrum (δ, DMSO-d$_6$):
3.54 (1H, d, J=18 Hz), 3.66 (1H, d, J=18 Hz),
4.21 (1H, d, J=14 Hz), 4.42 (1H, d, J=14 Hz),
4.99 (1H, d, J=5 Hz), 5.09 (2H, s),
5.11 (2H, s), 5.28 (2H, s),
5.60–5.86 (2H, m), 6.72 (2H, d, J=8 Hz),
7.26 (2H, d, J=8 Hz), 8.16 (1H, s),
8.32 (1H, s), 9.05 (1H, s),
9.40 (1H, d, J=8 Hz), 9.94 (1H, d, J=8 Hz)
Antibacterial activity (MIC, μg/ml):

| Staph. aureus 209-P | 12.5 |
| Escher. coli NIHJ | 1.56 |
| Kleb. pneumoniae EK-6 | ≦0.05 |
| Proteus morganii EP-14 | 3.13 |
| Pseud. aeruginosa EP-172 | 1.56 |
| Ser. marcescens ES-75 | 0.1 |

Preparation 3

Cephaloglycine (0.405 g) was suspended in 10 ml of ethyl acetate, and to the suspension was added 0.50 ml of N,O-bis(trimethylsilyl)acetamide at 0° C. with stirring. The mixture was stirred at room temperature for 1 hour. A suspension of 0.385 g of the acid chloride of Example 3 in ethyl acetate was added to the resulting solution at 0° C. with stirring, and the mixture was stirred at the same temperature for 1 hour. The solvent was distilled off, and the residue was dissolved in 5 ml of acetone. The solution was added dropwise to 70 ml of 0.25 N hydrochloric acid at 0° C. with stirring. The resulting precipitate was collected by filtration, washed with water, and then dried to afford 0.654 g of a crude product. The crude product was washed with ethyl ether, and dried to afford 0.600 g of the desired product.

Melting point: 142°–145° C. (decomp.)
Elemental analysis for $C_{34}H_{31}N_3O_{15}S$:

|  | C | H | N |
|---|---|---|---|
| Calculated (%): | 54.18 | 4.15 | 5.58 |
| Found (%): | 52.99 | 3.96 | 5.76 |

Infrared absorption spectrum (cm$^{-1}$, nujol):
1770, 1735, 1665, 1620.
NMR spectrum (δ, DMSO-d$_6$):
1.30 (6H, t, J=7 Hz), 2.00 (3H, s),
3.38 (1H, d, J=18 Hz), 3.48 (1H, d, J=18 Hz),
4.26 (4H, q, J=7 Hz), 4.64 (1H, d, J=14 Hz),
4.90 (1H, d, J=14 Hz), 4.98 (1H, d, J=5 Hz),
5.56–5.92 (2H, m), 7.20–7.54 (5H, m),
7.96 (1H, s), 8.14 (1H, s),
8.98 (1H, s), 9.44 (1H, d, J=8 Hz),
10.04 (1H, d, J=8 Hz)
Antibacterial activity (MIC, μg/ml)

| Staph. aureus 209-P | 0.4 |
| Escher. coli NIHJ | 3.13 |
| Kleb. pneumoniae EK-6 | ≦0.05 |
| Proteus morganii EP-14 | 12.5 |
| Pseud. aeruginosa EP-172 | 1.56 |

Ser. marcescens ES-75 0.2

Preparation 4

7β-[D-2-[6,7-Bis(ethoxycarbonyloxy)chromone-3-carboxamide]-2-(4-hydroxyphenyl)acetamide]-3-acetoxymethyl-3-cephem-4-carboxylic acid

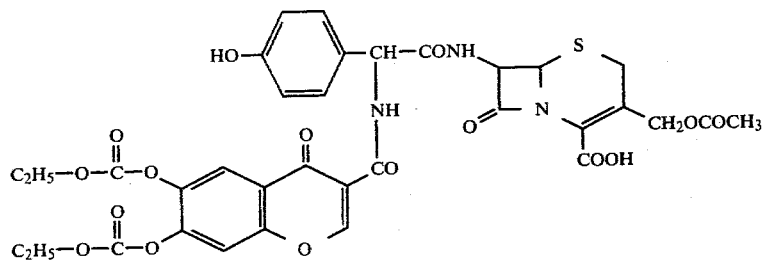

7β-[D-2-Amino-2-(4-hydroxyphenyl)acetamide]-3-acetoxymethyl-3-cephem-4-carboxylic acid (1.0 g) was suspended in 30 ml of tetrahydrofuran, and with stirring 2.0 ml of N,O-bis(trimethylsilyl)acetamide was added dropwise. The mixture was further stirred to form a solution. To the resulting solution was added a solution of 912 mg of the acid chloride of Example 3 in 5 ml of tetrahydrofuran under ice cooling. The mixture was stirred for 1 hour under ice cooling and then for 1 hour at room temperature. The reaction mixture was concentrated to 5 ml, and the concentrate was added dropwise to 20 ml of 0.5 N hydrochloric acid with stirring. The resulting precipitate was collected by filtration, washed with water, and then dissolved in ethyl acetate. The solution was washed with water three times, and dried over magnesium sulfate. The solvent was distilled off, and the residue was dissolved in 5 ml of ethyl acetate. The solution was added dropwise to 50 ml of ethyl ether with stirring. The resulting precipitate was collected by filtration, washed with ethyl ether and dried to afford 550 mg of the desired product.

Melting point: 213°–215° C. (decomp.)

Infrared absorption spectrum (cm$^{-1}$, nujol):
1785, 1770, 1735, 1680, 1660, 1620.

NMR spectrum (δ, DMSO-d$_6$):

1.31 (6H, t, J=7 Hz), 2.02 (3H, s),
3.3–3.6 (3H, bs), 4.31 (2H, q, J=7 Hz),
4.32 (2H, q, J=7 Hz), 4.65 (1H, d, J=14 Hz),
4.99 (1H, d, J=14 Hz), 5.03 (1H, d, J=4.5 Hz),
5.6–5.9 (2H, m), 6.72 (2H, d, J=8 Hz),
7.26 (2H, d, J=8 Hz), 8.04 (1H, s),
8.19 (1H, s), 9.36 (1H, d, J=8 Hz),
9.96 (1H, d, J=8 Hz)

What is claimed is:

1. Chromone derivatives having the formula:

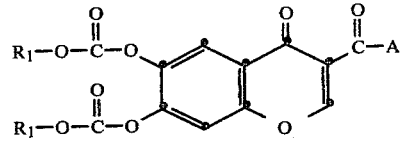

wherein A represents a hydrogen atom, a halogen atom or a hydroxyl group, and R$_1$ represents a lower alkyl or a chloro-substituted lower alkyl group.

2. Compound as claimed in claim 1, wherein the chromone derivative is 6,7-bis(ethoxycarbonyloxy)chromone-3-carboxaldehyde.

3. Compound as claimed in claim 1, wherein the chromone derivative is 6,7-bis(ethoxycarbonyloxy)chromone-3-carboxylic acid.

4. Compound as claimed in claim 1, wherein the chromone derivative is 6,7-bis(ethoxycarbonyloxy)chromone-3-carbonylchloride.

* * * * *